US012778382B2

(12) United States Patent
Liu et al.

(10) Patent No.: US 12,778,382 B2
(45) Date of Patent: Nov. 3, 2026

(54) BATTERY ASSEMBLY AND MEDICAL CAPSULE

(71) Applicants: Ankon Medical Technologies (Shanghai) Co., LTD., Shanghai (CN); ANX IP HOLDING PTE. LTD., Singapore (SG)

(72) Inventors: Lei Liu, Shanghai (CN); Hao Li, Shanghai (CN)

(73) Assignees: ANKON MEDICAL TECHNOLOGIES (SHANGHAI) CO., LTD, Shanghai (CN); ANX IP HOLDING PTE. LTD., Singapore (SG)

( * ) Notice: Subject to any disclaimer, the term of this patent is extended or adjusted under 35 U.S.C. 154(b) by 1003 days.

(21) Appl. No.: 18/007,731

(22) PCT Filed: May 28, 2021

(86) PCT No.: PCT/CN2021/096832
§ 371 (c)(1),
(2) Date: Jul. 18, 2023

(87) PCT Pub. No.: WO2021/244432
PCT Pub. Date: Dec. 9, 2021

(65) Prior Publication Data

US 2023/0346197 A1 Nov. 2, 2023

(30) Foreign Application Priority Data

Jun. 1, 2020 (CN) ......................... 202010486148.6

(51) Int. Cl.
*A61B 1/00* (2006.01)

(52) U.S. Cl.
CPC ........ *A61B 1/00032* (2013.01); *A61B 1/0011* (2013.01)

(58) Field of Classification Search
CPC .. H01M 50/548; H01M 50/55; H01M 50/216; H01M 50/24; H01M 50/247;
(Continued)

(56) References Cited

U.S. PATENT DOCUMENTS

| | | | | |
|---|---|---|---|---|
| 11,881,589 B2 * | 1/2024 | Shan | ................. | H01M 50/3425 |
| 2012/0028099 A1 * | 2/2012 | Aoki | .................. | H01M 10/643<br>429/120 |

(Continued)

FOREIGN PATENT DOCUMENTS

| | | | |
|---|---|---|---|
| CA | 2944366 C | * 12/2018 | ............ H01M 8/242 |
| CN | 102545310 A | 7/2012 | |

(Continued)

OTHER PUBLICATIONS

JP2004362957A—Lamination Type Cell Module, 15 pages. (Year: 2026).*

(Continued)

*Primary Examiner* — Tuyen K Vo
(74) *Attorney, Agent, or Firm* — Treasure IP Group, LLC

(57) ABSTRACT

There is provided a battery assembly and a medical capsule. The battery assembly comprises: a battery pack comprising at least two batteries connected in series, and a plurality of connectors electrically connected to the battery pack, comprising a positive electrode connector electrically connected to a positive electrode of the battery pack, a negative electrode connector electrically connected to a negative electrode of the battery pack, and an intermediate connector electrically connected to a positive electrode of one of any two adjacent batteries and a negative electrode of the other one of the two adjacent batteries. The battery assembly of the present invention can selectively output the total voltage of the battery pack or output part of the voltage of the battery pack through the plurality of connectors.

13 Claims, 5 Drawing Sheets

(58) Field of Classification Search
CPC .. H01M 50/296; H01M 50/502; H01M 50/51; H01M 50/516; H01M 4/34; H01M 6/04; H01M 6/12
See application file for complete search history.

(56) References Cited

U.S. PATENT DOCUMENTS

| | | | | |
|---|---|---|---|---|
| 2014/0141301 | A1* | 5/2014 | Aoki | H01M 10/425 429/90 |
| 2015/0155545 | A1 | 6/2015 | Baek | |
| 2015/0382501 | A1* | 12/2015 | Horiuchi | H05K 7/2089 363/131 |
| 2019/0259984 | A1* | 8/2019 | Nishikawa | H01M 50/247 |
| 2020/0153362 | A1* | 5/2020 | Xu | H03K 17/165 |
| 2020/0287251 | A1* | 9/2020 | Yonekura | G01R 31/3842 |

FOREIGN PATENT DOCUMENTS

| | | | |
|---|---|---|---|
| CN | 102646803 | A | 8/2012 |
| CN | 105877980 | A | 8/2016 |
| CN | 107847392 | A | 3/2018 |
| WO | 2012063854 | A1 | 5/2012 |

OTHER PUBLICATIONS

WO2018190235A1—Battery Module and Electricity Storage Unit, 59 pages. (Year: 2026).*

* cited by examiner

BATTERY ASSEMBLY AND MEDICAL CAPSULE

CROSS-REFERENCE OF RELATED APPLICATIONS

The application is a National Phase Application of PCT International Application No. PCT/CN2021/096832, International Filing Date May 28, 2021, which claims priority from Chinese Patent Application No. 202010486148.6, filed Jun. 1, 2020, all of which are incorporated herein by reference in their entireties.

FIELD OF INVENTION

The present invention relates to the field of medical device, and more particularly to a battery assembly a medical capsule capable of outputting various voltages.

BACKGROUND

With the development of science and technology, more advanced medical devices are developed for the diagnosis and treatment of human diseases. The development of ingestible medical devices represented by vibrating capsule and capsule endoscope greatly improves the comfort of treatment and avoids the occurrence of cross infection.

For ingestible medical capsules, a battery unit supplies power to other internal components. So, the safety, stability and other factors of the battery unit need to be comprehensively evaluated. At present, there are few large-capacity single-cell batteries that can meet the requirements of medical capsule devices, and basically only lithium batteries can be selected. However, the safety of lithium batteries in wide application needs to be verified.

Therefore, it is necessary to provide an improved battery assembly and medical capsule to solve the problem.

SUMMARY OF THE INVENTION

An object of the present invention is to provide a battery assembly and a medical capsule capable of outputting various voltages.

In order to achieve the object, the present invention uses the following technical solution:

a battery assembly, comprises:

a battery pack comprising at least two batteries connected in series; and a plurality of connectors electrically connected to the battery pack, comprising a positive electrode connector electrically connected to a positive electrode of the battery pack, a negative electrode connector electrically connected to a negative electrode of the battery pack, and an intermediate connector electrically connected to a positive electrode of one of any two adjacent batteries and a negative electrode of the other of the two adjacent batteries.

Further, the battery is a silver oxide battery.

Further, the connector is a nickel-plated SPCC steel sheet, a nickel sheet or a copper sheet.

Further, each of the positive electrode connector, the negative electrode connector and the intermediate connector comprises a welding portion welded to an electrode of the battery and an output portion connected to the welding portion.

Further, the output portion of the positive electrode connector and the output portion of the negative electrode connector extend towards a side of the positive electrode of the battery pack or a side of the negative electrode of the battery pack, and the output portion of the intermediate connector extends towards another side of the battery pack.

Further, the battery assembly further comprises an insulation assembly arranged between adjacent batteries or between the connector and the batteries.

Further, the insulation assembly comprises an insulation gasket disposed around the negative electrode of the battery.

Further, each of the positive electrode connector, the negative electrode connector and the intermediate connector comprises a welding portion welded to an electrode of the battery and an output portion connected to the welding portion. The output portion of the positive electrode connector and the output portion of the negative electrode connector extend towards a side of the positive electrode of the battery pack, and the output portion of the intermediate connector extends towards a side of the negative electrode of the battery pack. The insulation assembly further comprises a first insulation sheet disposed at one side of the output portion of the negative electrode connector facing the battery. When one battery is arranged between the welding portion of the intermediate connector and the negative electrode of the battery pack, an insulation sheet is or is not disposed on one side of the output portion of the intermediate connector facing the battery. When at least two batteries are arranged between the welding portion of the intermediate connector and the negative electrode of the battery pack, an insulation sheet is disposed on the side of the output portion of the intermediate connector facing the batteries.

Alternatively, each of the positive electrode connector, the negative electrode connector, and the intermediate connector comprises a welding portion welded to an electrode of the battery and an output portion connected to the welding portion; wherein the output portion of the positive electrode connector and the output portion of the negative electrode connector both extend towards a side of the negative electrode of the battery pack, and the output portion of the intermediate connector extends towards a side of the positive electrode of the battery pack; and wherein the insulation assembly also comprises a second insulation sheet and a third insulation sheet, wherein the second insulation sheet is disposed on one side of the output portion of the positive electrode connector facing the battery, and the third insulation sheet is disposed on one side of the output portion of the intermediate connector facing the battery.

In order to achieve the object, the present invention also uses the following technical solution:

a medical capsule comprises the battery assembly.

Further, the medical capsule is a vibrating capsule, and further comprises an enclosure, a vibration source and a control unit, wherein the vibration source and the control unit are housed in the enclosure, the control unit comprises a PCB, the positive electrode connector and the negative electrode connector are both electrically connected to the PCB, and the vibration source is electrically connected to both the PCB and the intermediate connector.

Further, the battery is a silver oxide battery.

Further, the connector is a nickel-plated SPCC steel sheet, a nickel sheet or a copper sheet.

Further, each of the positive electrode connector, the negative electrode connector and the intermediate connector comprises a welding portion welded to an electrode of the battery and an output portion connected to the welding portion.

Further, the output portion of the positive electrode connector and the output portion of the negative electrode connector extend towards a side of the positive electrode of the battery pack or a side of the negative electrode of the battery pack, and the output portion of the intermediate connector extends towards another side of the battery pack.

Further, the battery assembly further comprises an insulation assembly arranged between adjacent batteries or between the connector and the batteries.

Further, the insulation assembly comprises an insulation gasket disposed around the negative electrode of the battery.

Or, each of the positive electrode connector, the negative electrode connector and the intermediate connector comprises a welding portion welded to an electrode of the battery and an output portion connected to the welding portion; wherein the output portion of the positive electrode connector and the output portion of the negative electrode connector extend towards a side of the positive electrode of the battery pack, and the output portion of the intermediate connector extends towards a side of the negative electrode of the battery pack; wherein the insulation assembly further comprises a first insulation sheet disposed at one side of the output portion of the negative electrode connector facing the battery; wherein an insulation sheet is or is not disposed on one side of the output portion of the intermediate connector facing the battery when one battery is arranged between the welding portion of the intermediate connector and the negative electrode of the battery pack; and wherein an insulation sheet is disposed on the side of the output portion of the intermediate connector facing the batteries when at least two batteries are arranged between the welding portion of the intermediate connector and the negative electrode of the battery pack.

Or, each of the positive electrode connector, the negative electrode connector, and the intermediate connector comprises a welding portion welded to an electrode of the battery and an output portion connected to the welding portion; wherein the output portion of the positive electrode connector and the output portion of the negative electrode connector both extend towards a side of the negative electrode of the battery pack, and the output portion of the intermediate connector extends towards a side of the positive electrode of the battery pack; and wherein the insulation assembly also comprises a second insulation sheet and a third insulation sheet, wherein the second insulation sheet is disposed on one side of the output portion of the positive electrode connector facing the battery, and the third insulation sheet is disposed on one side of the output portion of the intermediate connector facing the battery.

In accordance with all aspects of the present invention, the battery assembly can output a total voltage of the battery pack through the positive electrode connector and the negative electrode connector, and can also output a voltage of part of the battery pack through the cooperation of one of the positive electrode or the negative electrode with the intermediate connector, so that different voltages can be provided to different electrical components and also different voltages can be provided to the same electrical component as required.

BRIEF DESCRIPTION OF THE DRAWINGS

In order to more clearly illustrate the technical solutions in the embodiments or prior art of the present invention, the following is a brief description of the accompanying drawings to be used in the description of the embodiments or prior art, and it will be apparent that the accompanying drawings in the following description are only embodiments of the present invention, and that other accompanying drawings may be obtained from the provided accompanying drawings without creative labor to a person of ordinary skill in the art.

Figure 1:
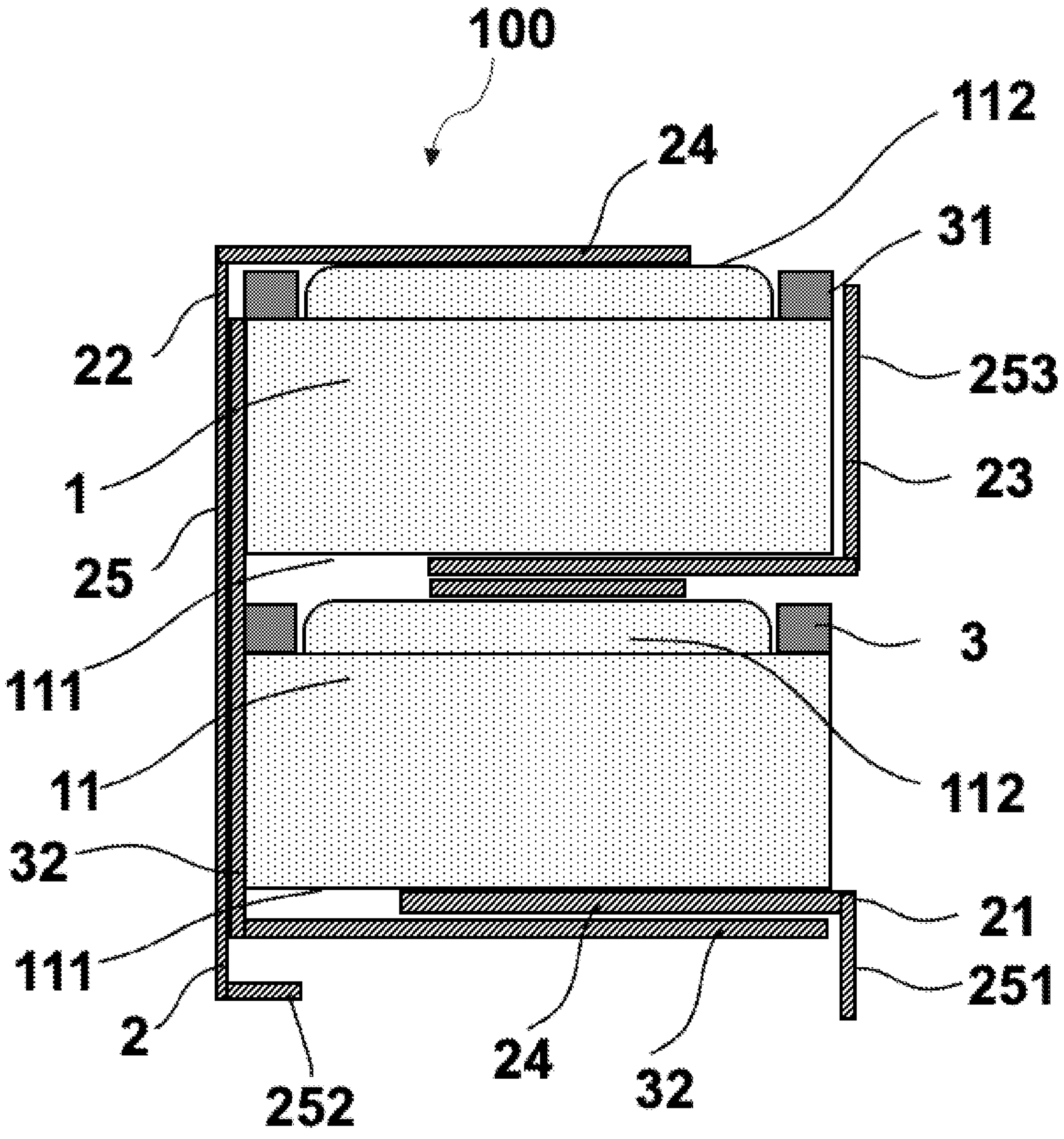
FIG. 1 is a structural diagram of a battery assembly according to a preferred embodiment of the present invention.

100—battery assembly; 1—battery pack, 11—battery, 111—positive electrode, 112—negative electrode, 2—connector, 21—positive electrode connector, 22—negative electrode connector, 23—intermediate connector, 24—welding portion, 25—output portion, 251—output portion of positive electrode connector, 252—output portion of negative electrode connector, 253—output portion of intermediate connector, 3—insulation assembly, 31—insulation gasket, 32—first insulation sheet, 200—medical capsule, 4—enclosure, 5—vibration source, 6—control unit, 61—PCB, 62—reed switch, 7—fixing structure.

DETAILED DESCRIPTION

The present invention is described in detail below with reference to the accompanying drawings and preferred embodiments. However, the embodiments are not intended to limit the invention, and the structural, method, or functional changes made by those skilled in the art in accordance with the embodiments are included in the scope of the present invention.

In the figures of the present invention, some dimensions of a structure or portion may be exaggerated relative to other structures or portions for ease of illustration, and thus, are merely used to illustrate the basic structure of the subject matter of the present invention.

Referring to FIGS. 1 to 5, in the embodiments of the present invention, a battery assembly 100 comprises a battery pack 1 and a plurality of connectors 2 electrically connected to the battery pack 1. The electrical connection may be realized by welding or conductive adhesive.

The battery pack 1 comprises at least two batteries 11 connected in series. Preferably, at least two batteries 11 are arranged in a stack, and the number of the batteries 11 can be adjusted according to a required output voltage.

In one embodiment, the battery 11 is a button type silver oxide battery, which is small in size, safe and stable enough to meet safety requirements of a medical capsule 200.

The plurality of connectors 2 comprises a positive electrode connector 21 electrically connected to a positive electrode 111 of the battery pack 1, a negative electrode connector 22 electrically connected to the negative electrode 112 of the battery pack 1, and an intermediate connector 23 electrically connected to both the positive electrode 111 and the negative electrode 112 of any two adjacent batteries 11. Therefore, the total voltage of the battery pack 1 can be output through the positive electrode connector 21 and the negative electrode connector 22, and the voltage of part of the battery pack 1 can be output through the cooperation of one of the positive electrode or the negative electrode with the intermediate connector 23, so as to supply power to different electrical components, or provide different voltages to the same electrical component as required.

"The voltage of part of the battery pack 1 can be output" means that the battery pack 1 comprises at least two batteries 11 connected in series, and the voltages of N batteries 11 are output through the cooperation of one of the positive electrode or the negative electrode with the intermediate connector 23, wherein N is an integer not greater than the total number of the batteries 11 contained in the battery pack 1. For example, the battery pack 1 comprises two batteries 11 connected in series, and can output the voltage of one battery 11. For example, the battery pack 1 comprises three batteries 11 connected in series, and can output different voltages of one battery 11, two batteries 11, or all three batteries 11.

The number of the batteries 11 connected in series between the intermediate connector 23 and the positive electrode connector 21 and the number of the batteries 11 connected in series between the intermediate connector 23 and the negative electrode connector 22 can be adjusted according to a required output voltage. For example, one battery 11 is connected in series between the intermediate connector 23 and the positive electrode connector 21, or one battery 11 is connected in series between the intermediate connector 23 and the negative electrode connector 22, so that the voltage of a single battery 11 can be output.

The connector 2 further comprises a welding portion 24 welded to the battery 11, and an output portion 25 connected to the welding portion 24. Generally, the welding portion 24 and the output portion 25 are integrally formed, and the output portion 25 can be bent into a desired shape to facilitate installation in the medical capsule 200. In this example, the connector 2 comprises the positive electrode connector 21, the negative electrode connector 22 and the intermediate connector 23.

Figure 2:
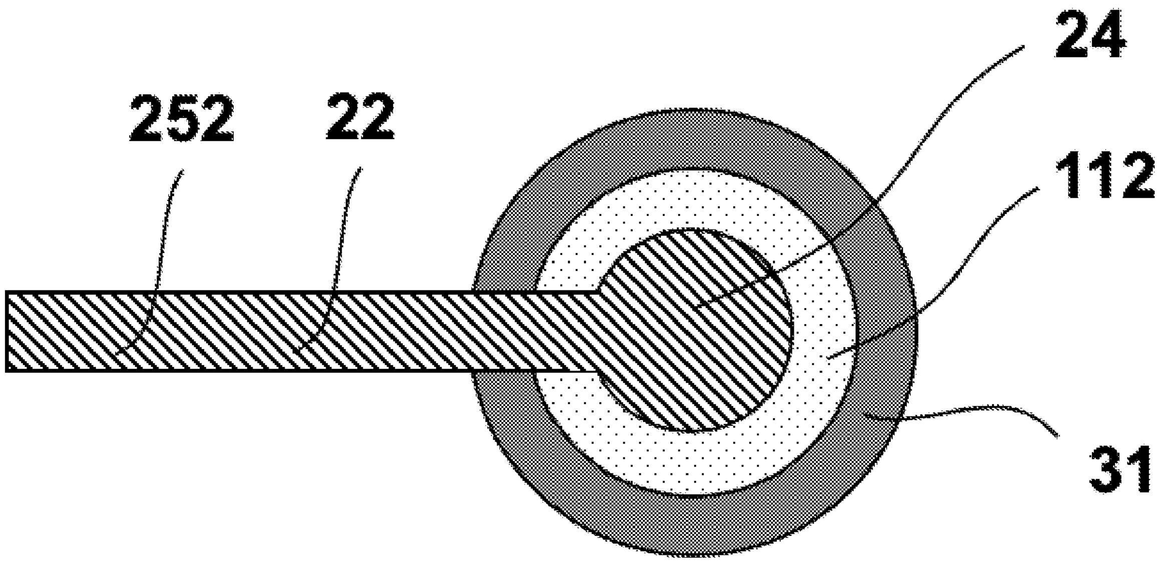
FIG. 2 is an assembly diagram of a negative electrode, an insulation sheet and a negative electrode connector of a battery in FIG. 1.
Figure 3:
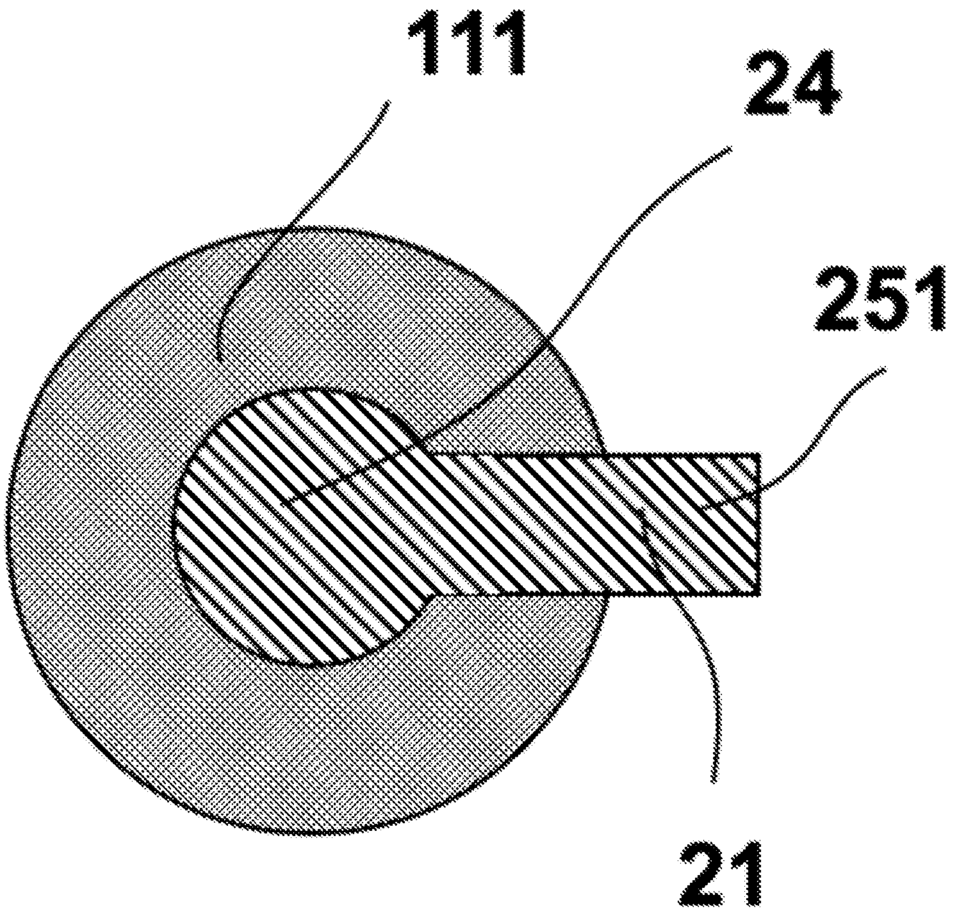
FIG. 3 is an assembly diagram of a positive electrode and a positive electrode connector of the battery in FIG. 1.

As shown in FIG. 1, FIG. 2 and FIG. 3, the structures of the positive electrode connector 21 and the negative electrode connector 22 are similar, and the welding portion 24 thereof is circular, which is convenient for multiple-point welding with the battery pack 1 and improves the welding stability. The welding portion 24 comprises a plurality of welding points, for example, the welding portion 24 comprises at least four welding points, which can be welded by soldering, high-pressure spot welding or laser spot welding to improve the stability of power supply. The output portions 251 and 252 are strip-shaped for easy bending.

In a preferred solution, the connector 2 is connected to the electrode of the battery 11 by a spot welding process, preferably by the laser spot welding, which features high consistency and high degree of automation. The connector 2 is welded to a printed circuit board (PCB) or a load electrical element by soldering, so as to maintain the stability of welding.

Figure 4:
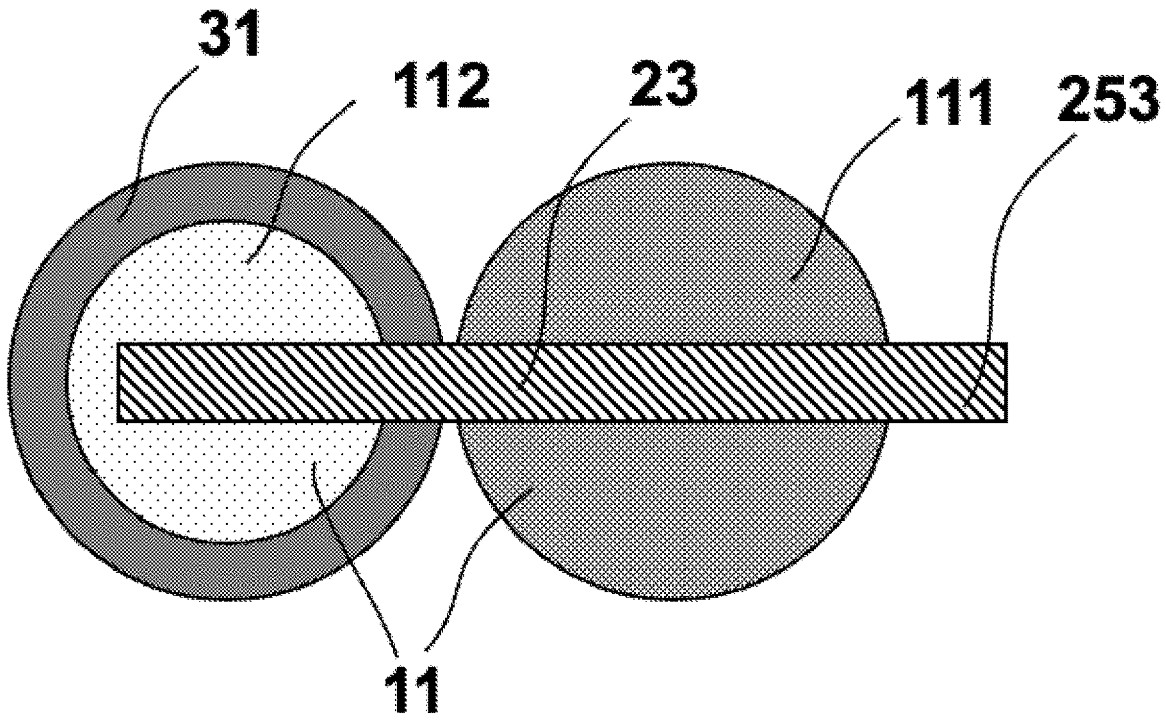
FIG. 4 is a schematic diagram illustrating an intermediate connector in FIG. 1 connected to the positive electrode and the negative electrode of two adjacent batteries respectively.
Figure 5:
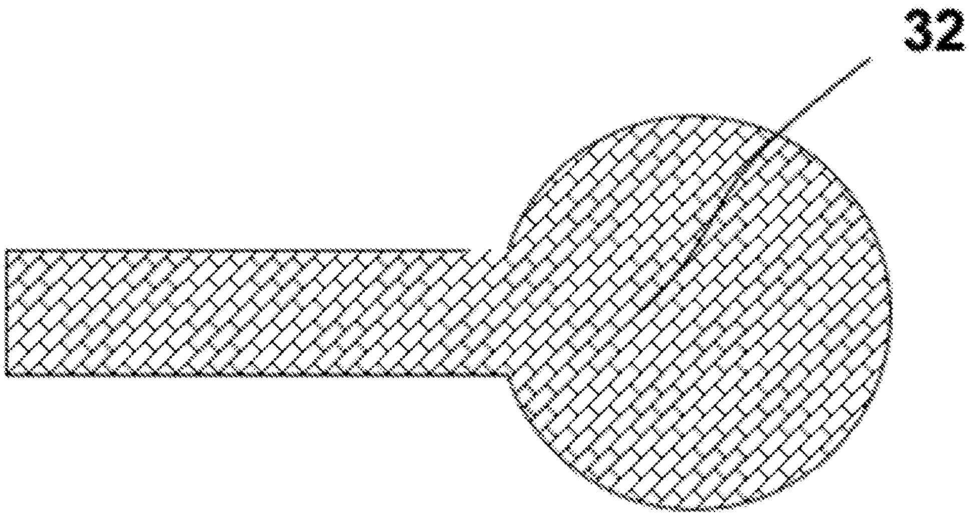
FIG. 5 is a structural diagram of a first insulation sheet.

Referring to FIG. 1 and FIG. 4, the intermediate connector 23 is strip-shaped, and the welding portion thereof is stacked between two adjacent batteries 11 after being welded to the two adjacent batteries 11.

Further, the connector 2 is a nickel-plated SPCC (Cold Rolled Steel, generally using cold-rolled carbon steel sheet and steel strip) steel sheet, a nickel sheet or a copper sheet, which can be welded to the electrode of the battery 11, the PCB and the load electrical element. Preferably, a pure nickel sheet is selected to effectively avoid cold solder joint. The pure nickel sheet is formed from pure nickel commonly mentioned in the industry, which is allowed to contain trace impurities that cannot be eliminated in the purification process, not referring to 100% pure nickel.

The output portion of the positive electrode connector 251 and the output portion of the negative electrode connector 252 extend towards a side of the positive electrode 111 of the battery pack 1 or a side of the negative electrode 112 of the battery pack 1, so as to be soldered to a same PCB. The output portion of the intermediate connector 253 extends towards another side of the battery pack 1. The output portion of the intermediate connector 253 is connected to a load electrical element, so as to cooperate with the PCB to output part of voltage of the whole battery pack 1 to the load electrical element. The set of the output portions 251, 252 and 253 can allow the battery pack 1 to output different voltages, and the different voltage can supply power to different electrical components to meet the power demand of different electrical components, or the different voltage can be supplied to a same electrical component to meet the power demand of the electrical component at different times.

In a specific embodiment, as shown in FIGS. 1 to 5, both the output portion of the positive electrode connector 251 and the output portion of the negative electrode connector 252 extend towards the side of the positive electrode 111 of the battery pack 1, so as to be soldered to the PCB. The output portion of the intermediate connector 253 extends towards the side of the negative electrode 112 of the battery pack 1.

Based on any of the above embodiments, the battery assembly 100 further comprises an insulation assembly 3, and those skilled in the art can understand that the insulation assembly 3 is disposed between two components requiring insulation to avoid short circuit. For example, the insulation assembly 3 is disposed between adjacent batteries 11, between the connector 2 and the battery 11, between the battery assembly 100 and an adjacent PCB, or between the battery assembly 100 and other adjacent electrical components.

Specifically, the insulation assembly 3 comprises an annular insulation gasket 31 located around the negative electrode 112 of the battery 11, which is adhered to the negative electrode 112 of the battery 11 and just covers the positive electrode part around the negative electrode 112 of the battery 11, so as to avoid short circuit between the positive electrode area and the negative electrode area of the battery 11 caused by devices or other electrical contacts. For example, the negative electrode 112 may be isolated from the positive electrode portion around the negative electrode 112, or the connector 2 connected to the negative electrode 112 may be isolated from the positive electrode portion around the negative electrode 112.

The insulation gasket 31 is a film made of polyethylene terephthalate (PET), polyvinyl chloride (PVC), polypropylene (PP), or polyamide (PA) with backing. The thickness of the insulation gasket 31 is 0.01 mm to 0.5 mm, preferably 0.05 mm to 0.15 mm, which can not only meet the requirements of high conformance rate, but also achieve good insulation characteristics.

As shown in FIGS. 1 to 5, the output portion of the positive electrode connector 251 and the output portion of the negative electrode connector 252 extend towards the side of the positive electrode 111 of the battery pack 1, and the output portion of the intermediate connector 253 extends towards the side of the negative electrode 112 of the battery pack 1. Insulation is required between the negative electrode connector 22 and the side wall of the battery pack 1. The insulation assembly 3 further comprises a first insulation sheet 32 disposed on a side of the output portion of the negative electrode connector 252 facing the battery 11, so as to insulate the negative electrode connector 22 from the side wall of the battery pack 1. Preferably, the first insulation sheet 32 is bent and extends to a side of the positive electrode connector 21 away from the battery pack 1, so as to insulate and separate the whole battery assembly 100 from the PCB.

In this embodiment, if there is only one battery 11 between the welding portion of the intermediate connector 23 and the negative electrode 112 of the battery pack 1, the output portion of the intermediate connector 253 does not need to be insulated from the side wall of the battery 11. Therefore, the side of the output portion of the intermediate connector 253 facing the battery 11 may or may not be provided with an insulation sheet. If there are at least two batteries 11 between the welding portion of the intermediate connector 23 and the negative electrode 112 of the battery pack 1, an insulation sheet should be disposed on the side of the output portion of the intermediate connector 253 facing the batteries 11 to avoid short circuit.

Alternatively, each of the output portion of the positive electrode connector 251 and the output portion of the negative electrode connector 252 extends towards the side of the negative electrode 112 of the battery pack 1, and the output portion of the intermediate connector 253 extends towards the side of the positive electrode 111 of the battery pack 1. The insulation assembly 3 further comprises a second insulation sheet disposed on a side of the output portion of the positive electrode connector 251 facing the battery 11, and a third insulation sheet disposed on a side of the output portion of the intermediate connector 253 facing the battery 11.

The battery assembly 100 of the present invention may be used with a variety of medical capsules 200 including, but not limited to, vibrating capsules, endoscopic capsules, etc.

Figure 6:
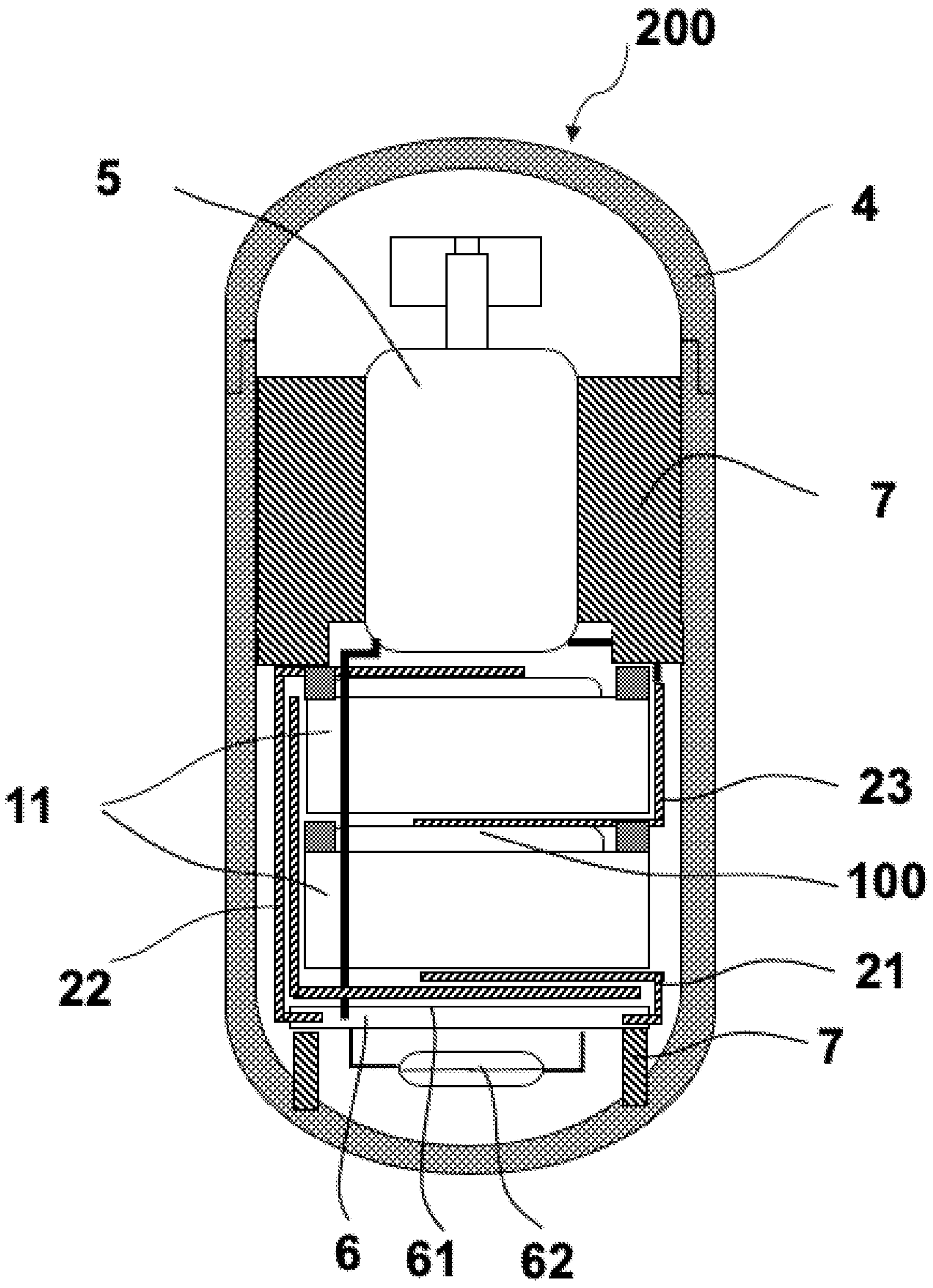
FIG. 6 is a structural diagram of a medical capsule according to a preferred embodiment of the present invention.

In one embodiment, referring to FIG. 6, the medical capsule 200 is a vibrating capsule, comprising an enclosure 4, a vibration source 5 housed in the enclosure 4, the battery assembly 100, and a control unit 6. The vibration source 5, the battery assembly 100 and the control unit 6 are fixed in the enclosure 4 by a fixing structure 7.

The enclosure 4 and the vibration source 5 are any one of the prior art, and the battery assembly 100 is any one of the above.

The control unit 6 comprises a PCB 61 and a reed switch 62 communicatively connected to the PCB 61. The positive electrode connector 21 and the negative electrode connector 22 are electrically connected to the PCB 61. The vibration source 5 is electrically connected to both the PCB 61 and the intermediate connector 23, so that different voltages can be output within the allowable voltage range of the vibration source 5.

In summary, the battery assembly 100 of the present invention can output the total voltage of the battery pack 1 through the positive electrode connector 21 and the negative electrode connector 22, and can also output part of the voltage of the battery pack 1 through the cooperation of one of the positive electrode or the negative electrode and the intermediate connector 23, to power different electrical components or to supply different voltages to the same electrical component as required.

It should be understood that, although the specification is described in terms of embodiments, not every embodiment merely comprises an independent technical solution. Those skilled in the art should have the specification as a whole, and the technical solutions in each embodiment may also be combined as appropriate to form other embodiments that can be understood by those skilled in the art.

The series of detailed descriptions set forth above are only specific to a feasible embodiment of the present invention and are not intended to limit the scope of protection of the present invention, and any equivalent embodiments or variations made without departing from the spirit of the art of the present invention shall be included within the scope of protection of the present invention.

The invention claimed is:

1. A battery assembly, comprises:

a battery pack comprising at least two batteries connected in series; and a plurality of connectors electrically connected to the battery pack, comprising a positive electrode connector electrically connected to a positive electrode of the battery pack, a negative electrode connector electrically connected to a negative electrode of the battery pack, and an intermediate connector electrically connected to a positive electrode of one of any two adjacent batteries and a negative electrode of the other of the two adjacent batteries;

wherein each of the positive electrode connector, the negative electrode connector and the intermediate connector comprises an output portion;

wherein the output portion of the positive electrode connector and the output portion of the negative electrode connector extend towards a side of the positive electrode of the battery pack or a side of the negative electrode of the battery pack, and the output portion of the intermediate connector extends towards another side of the battery pack.

2. The battery assembly of claim 1, wherein the battery is a silver oxide battery.

3. The battery assembly of claim 1, wherein the connector is a nickel-plated SPCC steel sheet, a nickel sheet or a copper sheet.

4. The battery assembly of claim 1, wherein each of the positive electrode connector, the negative electrode connector and the intermediate connector comprises a welding portion welded to an electrode of the battery and the output portion connected to the welding portion.

5. The battery assembly of claim 1, wherein the battery assembly further comprises an insulation assembly arranged between adjacent batteries or between the connector and the batteries.

6. The battery assembly of claim 5, wherein the insulation assembly comprises an insulation gasket disposed around the negative electrode of the battery;

or, each of the positive electrode connector, the negative electrode connector and the intermediate connector comprises a welding portion welded to an electrode of the battery and an output portion connected to the welding portion; wherein the output portion of the positive electrode connector and the output portion of the negative electrode connector extend towards a side of the positive electrode of the battery pack, and the output portion of the intermediate connector extends towards a side of the negative electrode of the battery pack; wherein the insulation assembly further comprises a first insulation sheet disposed at one side of the output portion of the negative electrode connector facing the battery; wherein an insulation sheet is or is not disposed on one side of the output portion of the intermediate connector facing the battery when one battery is arranged between the welding portion of the intermediate connector and the negative electrode of the battery pack; and wherein an insulation sheet is disposed on the side of the output portion of the intermediate connector facing the batteries when at least two batteries are arranged between the welding portion of the intermediate connector and the negative electrode of the battery pack;

or, each of the positive electrode connector, the negative electrode connector, and the intermediate connector comprises the welding portion welded to an electrode of the battery and the output portion connected to the welding portion; wherein the output portion of the positive electrode connector and the output portion of the negative electrode connector both extend towards the side of the negative electrode of the battery pack, and the output portion of the intermediate connector extends towards the side of the positive electrode of the battery pack; and wherein the insulation assembly also comprises a second insulation sheet and a third insulation sheet, wherein the second insulation sheet is disposed on one side of the output portion of the positive electrode connector facing the battery, and the third insulation sheet is disposed on the side of the output portion of the intermediate connector facing the battery.

7. A medical capsule, comprises the battery assembly of claim 1, the battery assembly comprising:

a battery pack comprising at least two batteries connected in series; and a plurality of connectors electrically connected to the battery pack, comprising a positive electrode connector electrically connected to a positive electrode of the battery pack, a negative electrode connector electrically connected to a negative electrode of the battery pack, and an intermediate connector electrically connected to a positive electrode of one of any two adjacent batteries and a negative electrode of the other of the two adjacent batteries;

wherein each of the positive electrode connector, the negative electrode connector and the intermediate connector comprises an output portion;

wherein the output portion of the positive electrode connector and the output portion of the negative electrode connector extend towards a side of the positive electrode of the battery pack or a side of the negative electrode of the battery pack, and the output portion of the intermediate connector extends towards another side of the battery pack.

8. The medical capsule of claim 7, wherein the battery is a silver oxide battery.

9. The medical capsule of claim 7, wherein the connector is a nickel-plated SPCC steel sheet, a nickel sheet or a copper sheet.

10. The medical capsule of claim 7, wherein each of the positive electrode connector, the negative electrode connector and the intermediate connector comprises a welding portion welded to an electrode of the battery and the output portion connected to the welding portion.

11. The medical capsule of claim 7, wherein the battery assembly further comprises an insulation assembly arranged between adjacent batteries or between the connector and the batteries.

12. The medical capsule of claim 11, wherein the insulation assembly comprises an insulation gasket disposed around the negative electrode of the battery;

or, each of the positive electrode connector, the negative electrode connector and the intermediate connector comprises a welding portion welded to an electrode of the battery and an output portion connected to the welding portion; wherein the output portion of the positive electrode connector and the output portion of the negative electrode connector extend towards a side of the positive electrode of the battery pack, and the output portion of the intermediate connector extends towards a side of the negative electrode of the battery pack; wherein the insulation assembly further comprises a first insulation sheet disposed at one side of the output portion of the negative electrode connector facing the battery; wherein an insulation sheet is or is not disposed on one side of the output portion of the intermediate connector facing the battery when one battery is arranged between the welding portion of the intermediate connector and the negative electrode of the battery pack; and wherein an insulation sheet is disposed on the side of the output portion of the intermediate connector facing the batteries when at least two batteries are arranged between the welding portion of the intermediate connector and the negative electrode of the battery pack;

or, each of the positive electrode connector, the negative electrode connector, and the intermediate connector comprises the welding portion welded to an electrode of the battery and the output portion connected to the welding portion; wherein the output portion of the positive electrode connector and the output portion of the negative electrode connector both extend towards the side of the negative electrode of the battery pack, and the output portion of the intermediate connector extends towards the side of the positive electrode of the battery pack; and wherein the insulation assembly also comprises a second insulation sheet and a third insulation sheet, wherein the second insulation sheet is disposed on one side of the output portion of the positive electrode connector facing the battery, and the third insulation sheet is disposed on the side of the output portion of the intermediate connector facing the battery.

13. The medical capsule of claim 7, wherein the medical capsule is a vibrating capsule, and further comprises an enclosure, a vibration source and a control unit, wherein the vibration source and the control unit are housed in the enclosure, the control unit comprises a PCB, the positive electrode connector and the negative electrode connector are both electrically connected to the PCB, and the vibration source is electrically connected to both the PCB and the intermediate connector.

* * * * *